United States Patent [19]

Glamkowski et al.

[11] Patent Number: 5,177,101

[45] Date of Patent: * Jan. 5, 1993

[54] MEMORY ENHANCING AND ANALGESIC AMINOCARBONYLCARBAMATES RELATED TO PHYSOSTIGMINE

[75] Inventors: Edward J. Glamkowski, Warren; Yulin Chiang, Convent Station; Russell R. L. Hamer, Lebanon, all of N.J.

[73] Assignee: Hoechst-Roussel Pharmaceuticals Incorporated, Somerville, N.J.

[*] Notice: The portion of the term of this patent subsequent to Dec. 31, 2008 has been disclaimed.

[21] Appl. No.: 749,083

[22] Filed: Aug. 23, 1991

Related U.S. Application Data

[63] Continuation of Ser. No. 443,682, Nov. 30, 1989, Pat. No. 5,077,289.

[51] Int. Cl.$^5$ .................. C07D 487/04; A61K 31/40
[52] U.S. Cl. ...................... 514/411; 548/429
[58] Field of Search ........................ 514/411; 548/429

[56] References Cited

U.S. PATENT DOCUMENTS

| | | | |
|---|---|---|---|
| 4,680,172 | 7/1987 | Leeson | 424/448 |
| 4,765,985 | 8/1988 | Leeson | 548/429 |
| 4,791,107 | 12/1988 | Hamer | 514/232.8 |
| 4,831,155 | 5/1989 | Brufani | 548/429 |
| 4,900,748 | 2/1990 | Brossi | 548/429 |

FOREIGN PATENT DOCUMENTS 154864 9/1985 European Pat. Off. .
298202 1/1989 European Pat. Off. .

OTHER PUBLICATIONS

Brossi, specification of SN166824.
Yu, Heterocycles 27, 745 (1988).
Yu, FEBS Letters 234, 127, 130 (1988).
Atack, J. Pharm. Exp. Ther. 249 194–202.
Fritz, Tetrahedron 26, 5821 (1970).

Primary Examiner—Mark L. Berch
Attorney, Agent, or Firm—Tatsuya Ikeda

[57] ABSTRACT

There are disclosed various derivatives related to physostigmine of the formula below,

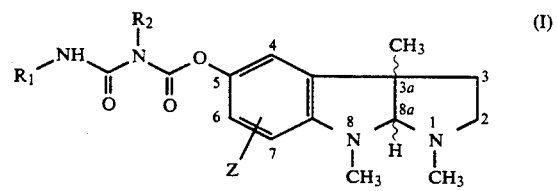

where Z, $R_1$ and $R_2$ are as defined in the specification, which compounds are useful for enhancing cholinergic function, and as analgesic agents.

4 Claims, No Drawings

MEMORY ENHANCING AND ANALGESIC AMINOCARBONYLCARBAMATES RELATED TO PHYSOSTIGMINE

This is a continuation of a prior application Ser. No. 443,682, filed Nov. 30, 1989 now U.S. Pat. No. 5,077,289.

The present invention relates to compounds of the formula,

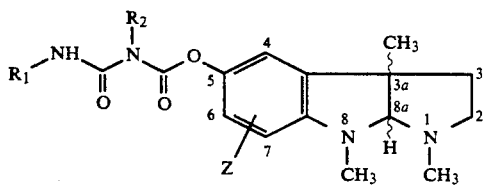

where
Z is hydrogen, halogen or loweralkyl;
$R_1$ is loweralkyl, cycloalkyl or aryl; and
$R_2$ is loweralkyl or cycloalkyl;
which compounds are useful for alleviating various memory dysfunctions characterized by a cholinergic deficit such as Alzheimer's disease and as analgesic agents.

Unless otherwise stated or indicated, the following definitions shall apply throughout the specification and the appended claims.

The term loweralkyl shall mean a straight or branched alkyl group having from 1 to 7 carbon atoms. Examples of said loweralkyl include methyl, ethyl, n-propyl, iso-propyl, n-butyl, iso-butyl, sec-butyl, t-butyl and straight- and branched-chain pentyl, hexyl and heptyl.

The term cycloalkyl shall mean a cycloalkyl group having from 3 to 7 carbon atoms in the ring. Said cycloalkyl group may be substituted with 1 or 2 loweralkyl groups.

The term halogen shall mean fluorine, chlorine, bromine or iodine.

The term aryl shall mean an unsubstituted phenyl group or a phenyl group mono-substituted with loweralkyl, halogen, nitro, loweralkoxy, hydroxy, or trifluoromethyl.

The compounds of this invention are prepared by utilizing the synthetic scheme described below.

In structural formulas depicting the compounds of this invention, heavy lines ( ▬ ) coming out of the 3a-carbon and 8a-carbon of the 1,2,3,3a,8,8a-hexahydropyrrolo[2,3-b]indole ring system signify that the two substituents are above the average plane of the three-ring system, whereas dotted lines ( ▬▬ ) signify that the two substituents are below the average plane of the three-ring system, and wavy lines ( ∿∿ ) signify that the two substituents are both either above or below said average plane. Because of conformational constraints, the two substituents at the 3a- and 8a-positions must be both above said average plane or both below said average plane. Thus, in formulas (I), (II) and (III), the substituents at the 3a- and 8a-carbons are cis inasmuch as they are on the same side of the three ring system. Where said substituents are both above the average plane of the three ring system, the configuration will be referred to as 3aS-cis and where both substituents are below the average plane of the ring, the configuration will be referred to as 3aR-cis. These two types of configuration are depicted below.

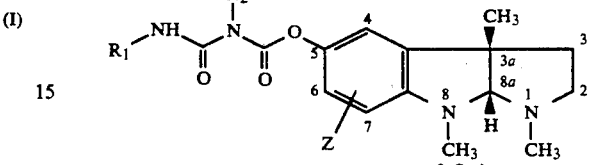

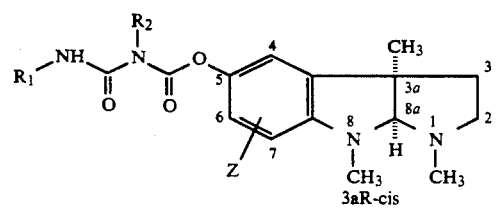

Throughout the specification and the appended claims, when the inventors intend to designate in a single formula (to save space) that the compound is 3aS-cis, or 3aR-cis, or a racemic or other mixture of the two, that formula will contain wavy lines as depicted below.

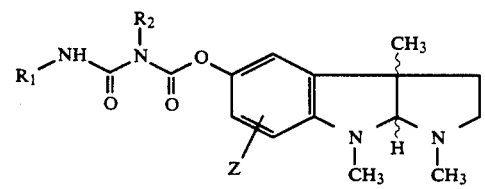

It is the intent of the present inventors to claim both of said cis isomers, namely, 3aS-cis isomer and 3aR-cis isomer for each compound name or structural formula although sometimes only one isomer is shown in the specification in order to save space. It is also the intent of the present inventors to claim all mixtures of the 3aS-cis and 3aR-cis isomers including the racemic mixture (1:1 ratio of 3aS-cis:3aR-cis).

SYNTHETIC SCHEME

Step A

Starting with a compound of formula II and utilizing the synthetic scheme disclosed in Julian et al., J. Chem. Soc., 1935, 563–566 and 755–757, one can prepare a compound of formula III as outlined in the diagram presented below. For details of the synthetic scheme, the reader is referred to the original articles.

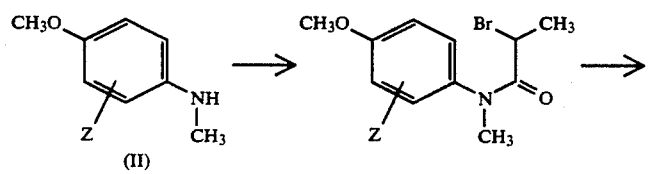

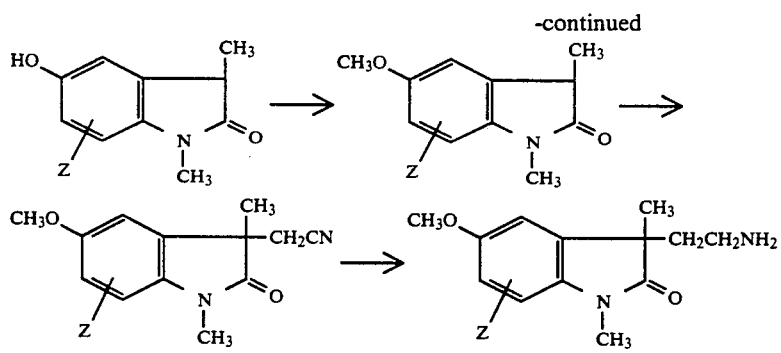

-continued

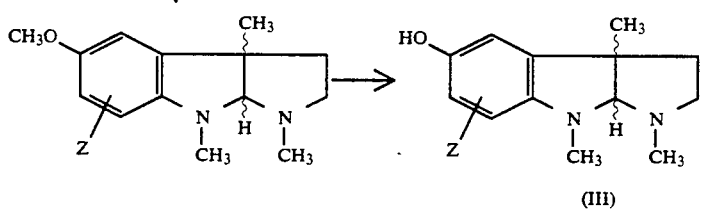

(1) C$_6$H$_5$CHO
(2) CH$_3$I
(3) hydrolysis
(4) Na/EtOH
(5) optical resolution (optional)

(III)

Step B

Where a target compound of formula I in which $R_1$ is the same as $R_2$ is desired, compound III is allowed to react with an isocyanate of the formula $R_1$NCO where $R_1$ is loweralkyl or cycloalkyl. It is preferable that the molar ratio between the isocyanate and compound III be at least 2:1. Typically, this reaction is conducted by adding a chip of Na metal to the reaction mixture and in the presence of a suitable solvent such as tetrahydrofuran or dichloromethane at a temperature of about 20° C. to the reflux temperature of the solvent.

(III) + R$_1$NCO ⟶

(Ia)

Step C

Where a target compound of formula I in which $R_1$ is not the same as $R_2$ is desired, compound III is allowed to react with an isocyanate of the formula R$_2$NCO to obtain a compound of formula IV in substantially the same manner as in STEP B except that the amount of the isocyanate is preferably about 1 equivalent relative to that of compound III. Subsequently, compound IV is allowed to react with another isocyanate of the formula R$_1$NCO in substantially the same manner as above to afford compound I.

(III) + R$_2$NCO ⟶

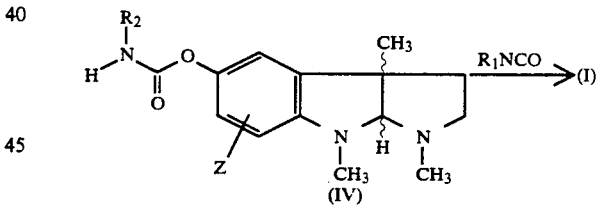

(IV)

The compounds of formula I of the present invention are useful for the treatment of various memory dysfunctions characterized by a decreased cholinergic function such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. Therefore, specific inhibitors of brain AChE (as opposed to serum AChE) will give rise to fewer side effects and thus lower toxicity than physostigmine (an unspecific AChE inhibitor). We have determined in vitro inhibition of acetylcholinesterase activity in rat striatum. Results of this assay for a representative compound of this invention and physostigmine (reference compound) are presented in Table 1.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anti-cholinesterase activity. This is a modification of the method of Ellman et al., Biochem. Pharmacol. 7, 98 (1961).

Procedure

A. Reagents 1. 0.05M Phosphate buffer, pH 7.2
 (a) 6.85 g $NaH_2PO_4 \cdot H_2O$/100 ml distilled $H_2O$
 (b) 13.40 g $Na_2HPO_4 \cdot 7H_2O$/100 ml distilled $H_2O$
 (c) add (a) to (b) until pH reaches 7.2
 (d) Dilute 1:10
2. Chromogen-substrate buffer
 (a) 9.9 mg 5,5-dithiobisnitrobenzoic acid (DTNB) (0.25 mM)
 (b) 99 mg S-acetylthiocholine chloride (5 mM)
 (c) q.s. to 100 ml with 0.05M phosphate buffer, pH 7.2 (reagent 1)
3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay

1. For routine $IC_{50}$ determinations the Abbott Bichromatic Analyzer, ABA-100, is used to determine acetylcholinesterase activity.

Instrument settings

Filter: 450-415
Incubation temperature: 30° C.
Decimal point: 0000.
Analysis time: 5 minutes
Carousel Revolution: 3

| Reaction direction | down |
| --- | --- |
| | endpoint |

Syringe plate: 1:101 dilution

Following the 10 minute preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.

2. The enzyme activity can also be measured with a Gilford 250 spectrophotometer. This method is used for more accurate kinetic measurements.

Instrument Settings

Lamp: visible
Filter: no filter
Wavelength: 412 nm
Slit width: 0.2 mm
Selection: small aperture
Calibrated absorbance: 1.0 unit full scale
Chart speed: 0.5 cm/min Reagents are added to the reference and sample side of a split curvette as follows:

| Reference | Sample |
| --- | --- |
| 0.8 ml 0.05M phosphate buffer | 0.8 ml 0.05M phosphate buffer |
| 0.8 ml Chromogen-substrate buffer | 0.8 ml Chromogen-substrate buffer |
| | 10 microliter enzyme (tissue homogenate) |

The uninhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/min) can be calculated as described in the following formula:

$$\text{rate (moles/liter/min)} = \text{slope}/(1.36 \times 10^4)$$

TABLE 1

| Compound | Inhibitory Concentration ($10^{-6}$M) Brain AChE |
| --- | --- |
| (3aS-cis)-1,2,3,3a,8,8a-hexahydro-1,3a,8-trimethyl-pyrrolo[2,3-b]indol-5-yl methyl[[(3-chlorophenyl)-amino]carbonyl]carbamate | 0.207 |
| (Reference Compound) Physostigmine | 0.034 |

This utility is further demonstrated by the ability of these compounds to restore cholinergically deficient memory in the Dark Avoidance Assay.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and physostigmine (reference compound) are presented in Table 2.

TABLE 2

| Compound | Dose (mg/kg of body weight, s.c.) | % of Animals with Scopolamine Induced Memory Deficity Reversal |
|---|---|---|
| (3aS-cis)-1,2,3,3a,8,8a-hexahydro-1,3a,8-trimethyl-pyrrolo[2,3-b]indol-5-yl propyl[(propylamino)-carbonyl] carbamate oxalate | 0.16 2.50 | 40% 36% |
| (3aS-cis)-1,2,3,3a,8,8a-hexahydro-1,3a,8-trimethyl-pyrrolo[2,3-b]indol-5-yl methyl[(methylamino)-carbonyl] carbamate | 0.16 | 20% |
| (Reference Compound) Physostigmine | 0.31 | 20% |

Compounds I of the present invention are also useful as analgesic agents due to their ability to alleviate pain in mammals. The activity of the compounds is demonstrated in the 2-phenyl-1,4-benzoquinone-induced writhing (PQW) test in mice, a standard assay for analgesics [Proc. Soc. Exptl. Biol. Med., 95, 729 (1957)].

Inhibition of Phenylquinone-Induced Writhing in Mice (PQW)

A 0.125% concentration of phenyl-p-benzoquinone in a 5% aqueous solution of ethyl alcohol is administered to mice (10 mL/kg,ip). This produces a characteristic "writhe" which is defined as an inward rotation of one or more feet with twisting and turning of the trunk, drawing in of the abdominal wall, lordosis, and arching of the back. A total of 28 male CD-1 Charles River mice (18-30 g) are employed for a time-response. Animals receive food and water ad libitum during their stay in the animal quarters prior to testing. Compounds are tested at 20 mg/kg, sc and are prepared with distilled water, and if insoluble one drop of Tween-80, a surfactant is added. Compounds are administered in a dosage volume of 10 mL/kg.

Twenty mice (five per group) are administered the test compound at various pretreat time (e.g., 15, 30, 45, and 60 min) prior to phenylquinone injection. Control animals (two per group) receive an equal volume of vehicle. After the administration of phenylquinone, the mice are placed separately into 1-L beakers, and 5 min are allowed to elapse. The mice are then observed for a period of 10 min, and the number of writhes is recorded for each animal. The formula for computing percent inhibition is $$\frac{(\overline{X} \text{ writhes in control group}) - (\overline{X} \text{ writhes in drug group})}{\overline{X} \text{ writhes in control group}} \times 100\%$$

The time period with the maximum percent of inhibition is considered the peak time. A dose-response is reserved for interesting compounds or those which inhibit writhing by 70% or more. A dose-response is run in the same manner as a time-response except 10 animals per group are tested at the peak time of drug activity. Fifty animals, divided among four drug groups and one vehicle control group, are employed. The mice are normally given four doses of drug, each twice the amount of the preceding dose. An $ED_{50}$ is calculated by a computer linear regression analysis.

Results of this assay for some of the compounds of this invention and eseroline salicylate (reference compound) are shown in Table 3.

TABLE 3

ANALGESIC ACTIVITY

| Compound | PQW (mg/kg, s.c.) |
|---|---|
| (3aS-cis)-1,2,3,3a,8,8a-hexahydro-1,3a,8-trimethyl-pyrrolo[2,3-b]indol-5-yl methyl[(methylamino)carbonyl] carbamate | 8.0 |
| (3aS-cis)-1,2,3,3a,8,8a-hexahydro-1,3a,8-trimethyl-pyrrolo[2,3-b]indol-5-yl methyl[[3-chlorophenyl)amino]-carbonyl] carbamate | 0.15 |
| (3aS-cis)-1,2,3,3a,8,8a-hexahydro-1,3a,7,8-tetramethyl-pyrrolo[2,3-b]indol-5-yl methyl[(methylamino)carbonyl] carbamate | 0.81 |
| (Reference Compound) Eseroline Salicylate | 0.52 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of the invention include those listed below as well as the 3aR-cis isomers thereof and mixtures of the 3aS-cis and 3aR-cis isomers including the racemic mixtures:

(3aS-cis)-1,2,3,3a,8,8a-hexahydro-1,3a,8-trimethylpyrrolo[2,3-b]indol-5-yl methyl[(methylamino)carbonyl] carbamate;
(3aS-cis)-1,2,3,3a,8,8a-hexahydro-1,3a,7,8-tetramethylpyrrolo[2,3-b]indol-5-yl methyl[(methylamino)carbonyl] carbamate;
(3aS-cis)-7-bromo-1,2,3,3a,8,8a-hexahydro-1,3a,8-trimethylpyrrolo[2,3-b]indol-5-yl methyl[(methylamino)carbonyl] carbamate;
(3aS-cis)-1,2,3,3a,8,8a-hexahydro-1,3a,8-trimethylpyrrolo[2,3-b]indol-5-yl propyl[(propylamino)carbonyl] carbamate;
(3aS-cis)-1,2,3,3a,8,8a-hexahydro-1,3a,8-trimethylpyrrolo[2,3-b]indol-5-yl methyl[[(3-chlorophenyl)amino]carbonyl] carbamate;
(3aS-cis)-1,2,3,3a,8,8a-hexahydro-1,3a,8-trimethylpyrrolo[2,3-b]indol-5-yl heptyl[(heptylamino)carbonyl] carbamate;
(3aS-cis)-1,2,3,3a,8,8a-hexahydro-1,3a,8-trimethylpyrrolo[2,3-b]indol-5-yl methyl[(heptylamino)carbonyl] carbamate;
(3aS-cis)-1,2,3,3a,8,8a-hexahydro-1,3a,8-trimethylpyrrolo[2,3-b]indol-5-yl methyl[(cyclohexylamino)carbonyl] carbamate;
(3aS-cis)-1,2,3,3a,8,8a-hexahydro-1,3a,8-trimethylpyrrolo[2,3-b]indol-5-yl heptyl[(propylamino)carbonyl] carbamate;
(3aS-cis)-1,2,3,3a,8,8a-hexahydro-1,3a,8-trimethylpyrrolo[2,3-b]indol-5-yl methyl[(phenylamino)carbonyl] carbamate;
(3aS-cis)-1,2,3,3a,8,8a-hexahydro-1,3a,8-trimethylpyrrolo[2,3-b]indol-5-yl methyl[[(4-methylphenyl)amino]carbonyl] carbamate;
(3aR-cis)-1,2,3,3a,8,8a-hexahydro-1,3a,8-trimethylpyrrolo[2,3-b]indol-5-yl methyl[[(3-chlorophenyl)amino]carbonyl] carbamate; and
cis-($\pm$)-1,2,3,3a,8,8a-hexahydro-1,3a,8-trimethylpyrrolo[2,3-b]indol-5-yl propyl[(propylamino)carbonyl] carbamate.

The following examples are presented in order to illustrate this invention.

EXAMPLE 1

(3aS-cis)-1,2,3,3a,8,8a-Hexahydro-1,3a,8-trimethylpyrrolo[2,3-b]indol-5-yl methyl[(methylamino)carbonyl] carbamate A degassed solution of physostigimine (3.0 g) in tetrahydrofuran (13 ml) was treated with methyl isocyanate (1.3 ml) and a chip of sodium metal under $N_2$ at room temperature. The mixture was stirred at room temperature for 18 hours, and thereafter heated at 45° C. for 3.5 hours. At the end of the reaction period, the solution was concentrated down to an oily foam, and the crude product was purified by flash chromatography over a silica gel column. The resultant solid product (1.3 g) was recrystallized from dichloromethane (4 ml) and isopropyl ether (40 ml) to provide crystals, 1.03 g, m.p. 157°–158° C.

Analysis: Calculated for $C_{17}H_{24}N_4O_3$: 61.43% C, 7.28% H, 16.85% N. Found: 61.31% C, 7.26% H, 16.80% N.

EXAMPLE 2

(3aS-cis)-1,2,3,3a,8,8a-Hexahydro-1,3a,7,8-tetramethylpyrrolo[2,3-b] indol-5-yl methyl[(methylamino)carbonyl] carbamate A degassed solution of 7-methyl eseroline (500 mg) in tetrahydrofuran (8 ml) was treated with a chip of sodium (~3 mg) and methyl isocyanate (0.7 ml) at room temperature for 20 minutes. The reaction was monitored on a TLC plate. The sodium chip was removed, and the solution was concentrated to dryness. The residue was extracted into ether (100 ml) and the insolubles were filtered. The crude product from ether was purified by flash chromatography over a silica gel column. The oily product thus obtained (400 mg) was dissolved in ether (30 ml) and filtered once, and thereafter concentrated back to oil. The oil solidified in isopropyl ether (1 ml). Recrystallization of the solid from isopropyl ether (4 ml) gave crystals (358 mg), m.p. 147°–149° C.

Analysis: Calculated for $C_{18}H_{26}N_4O_3$: 62.41% C, 7.56% H, 16.17% N. Found: 62.40% C, 7.59% H, 16.08% N.

EXAMPLE 3

(3aS-cis)-7-Bromo-1,2,3,3a,8,8a-hexahydro-1,3a,8-trimethylpyrrolo[2,3-b]indol-5-yl methyl[(methylamino)carbonyl] carbamate hemihydrate A solution of 7-bromo physostigmine (1.87 g) in tetrahydrofuran (20 ml) was charged with methyl isocyanate (1.0 g) and a catalytic amount of sodium. The mixture was heated overnight at 50° C. The reaction solution was concentrated to an oil. The oil was purified by flash chromatography twice on a silica gel column. The purest fractions were combined to give a colorless oil (650 mg). Crystallization from a small amount of ether yielded 420 mg of crystals, m.p. 105°–108° C. This material appeared to be the hemihydrate and was pure by TLC over $SiO_2$ plates.

Analysis: Calculated for $C_{17}H_{23}BrN_4O_3 \cdot 0.5H_2O$: 48.58% C, 5.75% H, 13.33% N. Found: 48.56% C, 5.70% H, 13.16% N.

EXAMPLE 4

(3aS-cis)-1,2,3,3a,8,8a-Hexahydro-1,3a,8,-trimethylpyrrolo[2,3-b]indol-5-yl propyl[(propylamino)carbonyl] carbamate oxalate A solution of eseroline (1.7 g) and n-propyl isocyanate (1.5 g, 2.2 equiv.) in 50 ml of degassed dry tetrahydrofuran was treated with a chip of sodium metal (0.2 g) and stirred at ambient temperature. After 16 hours, the solution was heated at reflux for 4 hours and thereafter concentrated. The residue was purified by flash chromatography to give 2.1 g of oil. This oil was taken up in ether and treated with oxalic acid (0.8 g) and concentrated. The residue was recrystallized from methanol/ether to give 1.9 g of crystals, m.p. 125°–127° C.

Analysis: Calculated for $C_{21}H_{32}N_4O_3 \cdot C_2H_2O_4$: 57.72% C, 7.16% H, 11.71% N. Found: 57.72% C, 7.44% H, 11.76% N.

EXAMPLE 5

(3aS-cis)-1,2,3,3a,8,8a,-Hexahydro-1,3a,8-trimethylpyrrolo-[2,3-b]indol-5-yl methyl[[(3-chlorophenyl)amino]carbonyl] carbamate A degassed solution of physostigmine (2.75 g) in tetrahydrofuran (30 ml) was charged with 3-chlorophenyl isocyanate (1.65 g, 1.1 equiv.) and a small chip of sodium. The mixture was stirred for 1 hour and concentrated to a foam. The residue was triturated with ether and filtered. The solid was recrystallized from dichloromethane/isopropyl ether (10 ml:10 ml) to give 3.4 g, m.p. 144°–146° C.

Analysis: Calculated for $C_{22}H_{25}ClN_4O_3$: 61.61% C, 5.88% H, 13.06% N. Found: 61.31% C, 5.91% H, 12.94% N.

We claim:

1. A compound of the formula

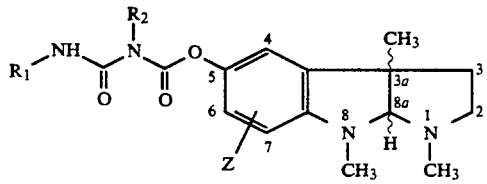

where
Z is halogen;
$R_1$ is phenyl or loweralkylphenyl; and
$R_2$ is loweralkyl or cycloalkyl;
the 3aS-cis isomer or the 3aR-cis isomer thereof or a mixture of the two isomers including the racemic mixture, or a pharmaceutically acceptable acid addition salt thereof.

2. A pharmaceutical composition comprising a compound as defined in claim 1 in an amount effective for alleviating a memory dysfunction characterized by a cholinergic deficit or for alleviating pain and a suitable carrier therefor.

3. A method of treating a patient in need of relief from a memory dysfunction characterized by a cholinergic deficit which comprises administering to such a patient an effective amount of a compound as defined in claim 1.

4. A method of treating a patient in need of relief from pain which comprises administering to such a patient an effective amount of a compound as defined in claim 1.

* * * * *